(12) United States Patent
Barberi et al.

(10) Patent No.: US 10,090,781 B2
(45) Date of Patent: Oct. 2, 2018

(54) PIEZOELECTRIC MOTOR ASSEMBLY

(71) Applicant: MODUS MEDICAL DEVICES INC., London (CA)

(72) Inventors: Enzo Antonio Barberi, London (CA); David John Munro Miller, London (CA); Jennifer Michele Dietrich, London (CA); Nicholas Gerard Hartman, Parkhill (CA)

(73) Assignee: MODUS MEDICAL DEVICES INC., London, Ontario (CA)

( * ) Notice: Subject to any disclaimer, the term of this patent is extended or adjusted under 35 U.S.C. 154(b) by 154 days.

(21) Appl. No.: 15/406,164

(22) Filed: Jan. 13, 2017

(65) Prior Publication Data

US 2017/0207726 A1 Jul. 20, 2017

Related U.S. Application Data

(60) Provisional application No. 62/278,637, filed on Jan. 14, 2016.

(51) Int. Cl.
*H02N 2/10* (2006.01)
*H02N 2/12* (2006.01)
*G01R 33/58* (2006.01)
*H01L 41/09* (2006.01)

(52) U.S. Cl.
CPC .............. *H02N 2/103* (2013.01); *G01R 33/58* (2013.01); *H01L 41/09* (2013.01); *H02N 2/123* (2013.01)

(58) Field of Classification Search
CPC ........ H02N 2/103; H02N 2/123; G01R 33/58; H01L 41/09
See application file for complete search history.

(56) References Cited

U.S. PATENT DOCUMENTS

| | | | |
|---|---|---|---|
| 2007/0194660 A1* | 8/2007 | Hashimoto | G04C 3/12 310/316.01 |
| 2009/0257139 A1* | 10/2009 | Shiga | G02B 7/023 359/824 |
| 2013/0158565 A1* | 6/2013 | Anvari | A61B 10/0266 606/130 |

* cited by examiner

*Primary Examiner* — Rodney Bonnette

(57) ABSTRACT

A piezoelectric motor assembly for producing rotary motion, according to the present invention, has a motor frame and a circular body rotatably mounted on the motor frame having a diameter, a thickness, and a circumferential outer surface. At least two piezoelectric motors are mounted on the motor frame in tangential engagement with the outer surface of the circular body. The at least two piezoelectric motors are biased against the outer surface, resulting in an unbalanced net force on the circular body.

14 Claims, 6 Drawing Sheets

PIEZOELECTRIC MOTOR ASSEMBLY

FIELD OF THE INVENTION

The present invention relates to rotary motors, in particular, to a piezoelectric motor assembly for producing rotary motion.

BACKGROUND

Piezoelectric motors are frequently employed in applications which require non-ferrous, non-magnetic motion control, such as to drive the motion of MRI motion phantoms within a MRI system. In these applications, motors that generate torque from the interaction of large currents and permanent magnets are generally unsuitable and/or dangerous to use in the vicinity of the high magnetic field of MRI systems. Use of these types of motors, such as stepper motors, induction motors, and electromagnetic motors, results in undesirable interactions between the MRI magnetic field and the ferrous material required for motor function.

Piezoelectric motors are compatible and safe for use inside low and high strength MRI systems. This is because they are based on voltage driven piezoelectric transducers, which can be designed and built without the use of ferrous materials. Piezoelectric motors operate based on the material properties of piezoelectric materials, typically a polled ceramic or polymer. These materials are exposed to an extremely powerful electric field to polarize the ceramic or polymer material, inducing a permanent electric field bias within the material structure.

This permanent electric field bias of a piezoelectric material causes the material to react mechanically to an applied voltage across the material. The material reacts in a linear fashion. Consequently, piezoelectric motors are generally well suited to producing linear motion.

Currently available rotary piezoelectric motor assemblies translate the linear motion from piezoelectric motors to a rotary motion, but are limited to low speed and/or low torque applications. Such rotary piezoelectric motor assemblies typically use one or two linear motors arranged about a rotary stage bearing. The inherent speed and force limitations of piezoelectric motors requires the use of more than one motor when high speed and torque are required. Where two or more motors are used, two main challenges arise in operating the motors cooperatively, namely, resonance and dissonance between the piezoelectric motors. Generally, resonance stores energy within the motor and rotary stage system, which can be released in undesired ways, causing vibration when the motors are engaged. Dissonance, on the other hand, results from interference between the piezoelectric motors due to small differences in mechanical feedback induced to each motor, causing noise, vibration, and harshness and reducing the speed, torque, efficiency, and life of the rotary motor.

Accordingly, there is a need for a piezoelectric motor assembly that permits the efficient translation of linear motion from a plurality of piezoelectric motors into rotary motion, while minimizing mechanical drive assembly resonance and dissonance therebetween.

SUMMARY OF THE INVENTION

A piezoelectric motor assembly for producing rotary motion, according to the present invention, has a motor frame and a circular body rotatably mounted on the motor frame having a diameter, a thickness, and a circumferential outer surface. At least two piezoelectric motors are mounted on the motor frame in tangential engagement with the outer surface of the circular body. The at least two piezoelectric motors are biased against the outer surface to result in an unbalanced net force on the circular body.

In one embodiment, the at least two piezoelectric motors are horizontally spaced apart on the outer surface of the circular body.

In another embodiment, the at least two piezoelectric motors are horizontally spaced apart along an arc subtending an angle of less than 180 degrees.

In another embodiment, the at least two piezoelectric motors are spaced apart vertically on the outer surface of the circular body.

According to another aspect of the present invention, a combination of a MRI compatible piezoelectric motor assembly and a MRI motion phantom, for use in a MRI system, has a piezoelectric motor assembly with a motor frame mounted in a housing. A circular body rotatably mounted on the motor frame, having a diameter, a thickness, and a circumferential outer surface. At least two piezoelectric motors are mounted on the motor frame in tangential engagement with the outer surface of the circular body. The at least two piezoelectric motors are biased against the outer surface, resulting in an unbalanced net force on the circular body. A drive hub rigidly mounted to the circular body by way of a drive shaft and spaced apart therefrom, having a drive pin extending from the drive hub parallel to the drive shaft and radially offset therefrom. A translation stage slidably mounted on the housing adjacent the drive hub so as to slide freely in a first direction perpendicular to the drive shaft, having a slot-shaped aperture therethrough perpendicular to the first direction and the drive shaft, wherein the drive pin extends through the slot-shaped aperture to thereby drive the motion of the translation stage in the first direction as the drive hub rotates. A pivot arm pivotally mounted at a first end to the translation stage and connected to the drive pin at a second end by a ball joint to thereby pivot the pivot arm as the drive pin moves back and forth within the slot-shaped aperture in the second direction. A spindle axially aligned with the first direction and selectively rotatably mounted on the translation stage, so as to move axially with the translation stage, and selectively rotatably attached to the first and of the pivot arm to selectively receive rotation therefrom. The MRI motion phantom has a container containing a first MRI signal producing material and having an aperture through the container for receiving a MRI insert. A MRI insert is attached to the spindle and slidably and rotatably mounted within the aperture in the container, and contains a second MRI signal producing material.

BRIEF DESCRIPTION OF THE DRAWINGS

In order that the invention may be more clearly understood, a preferred embodiment thereof will now be described in detail by way of example, with reference to the accompanying drawings, in which.

DESCRIPTION OF THE PREFERRED EMBODIMENT

A piezoelectric motor assembly for producing rotary motion, according to the present invention, uses at least two piezoelectric motors tangentially arranged about a circular body and biased against the outer surface thereof, resulting in an unbalanced net force on the circular body. The motor assembly may be used, for example, to drive reciprocating linear motion and rotational motion of a moving insert in a MRI motion phantom. Providing such inserts with both linear and rotational motion helps provide a more realistic motion, for example to simulate the movement of a target within the breathing lung of a patient.

Figure 1:
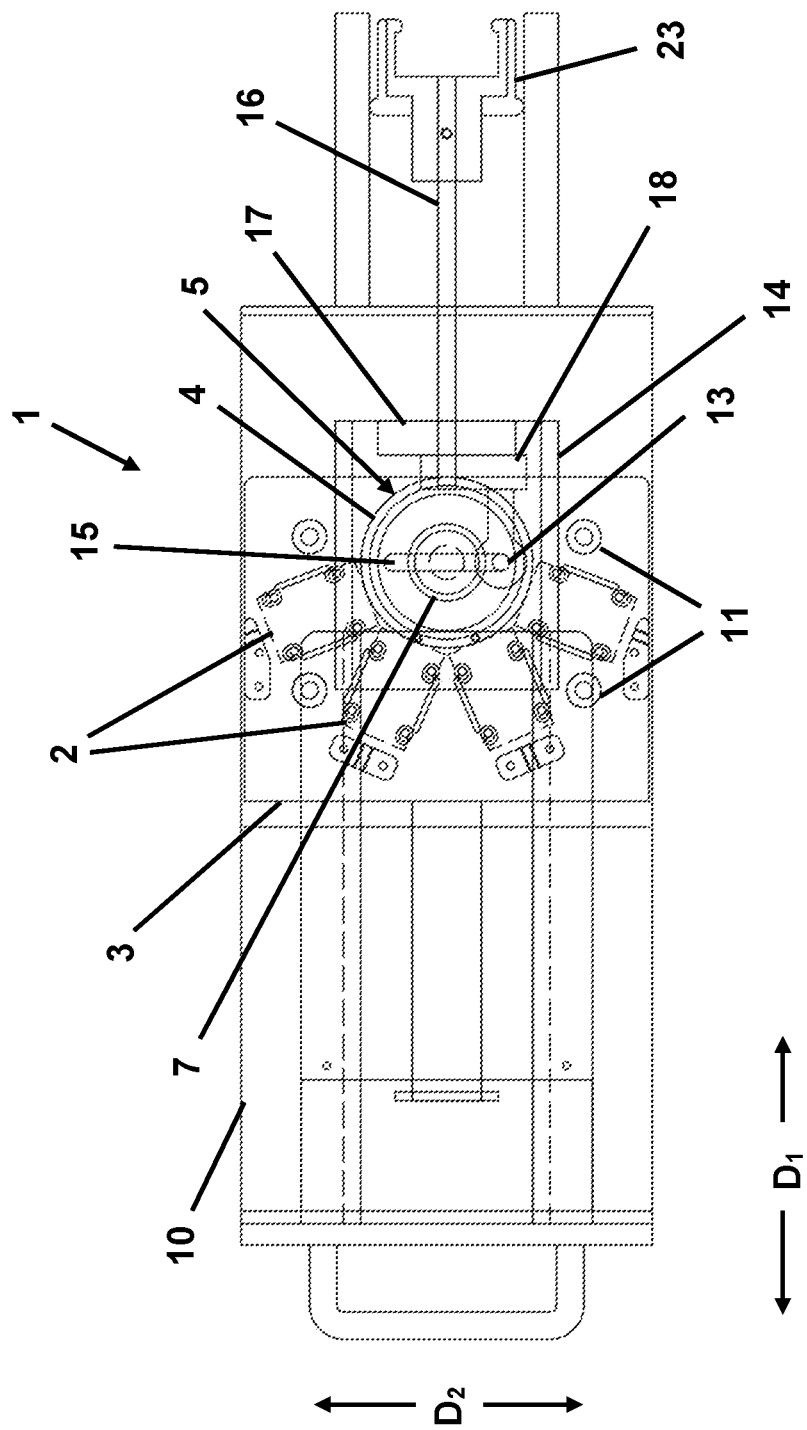
FIG. 1 is a schematic top view of a piezoelectric motor assembly, according to the present invention.
Figure 2:
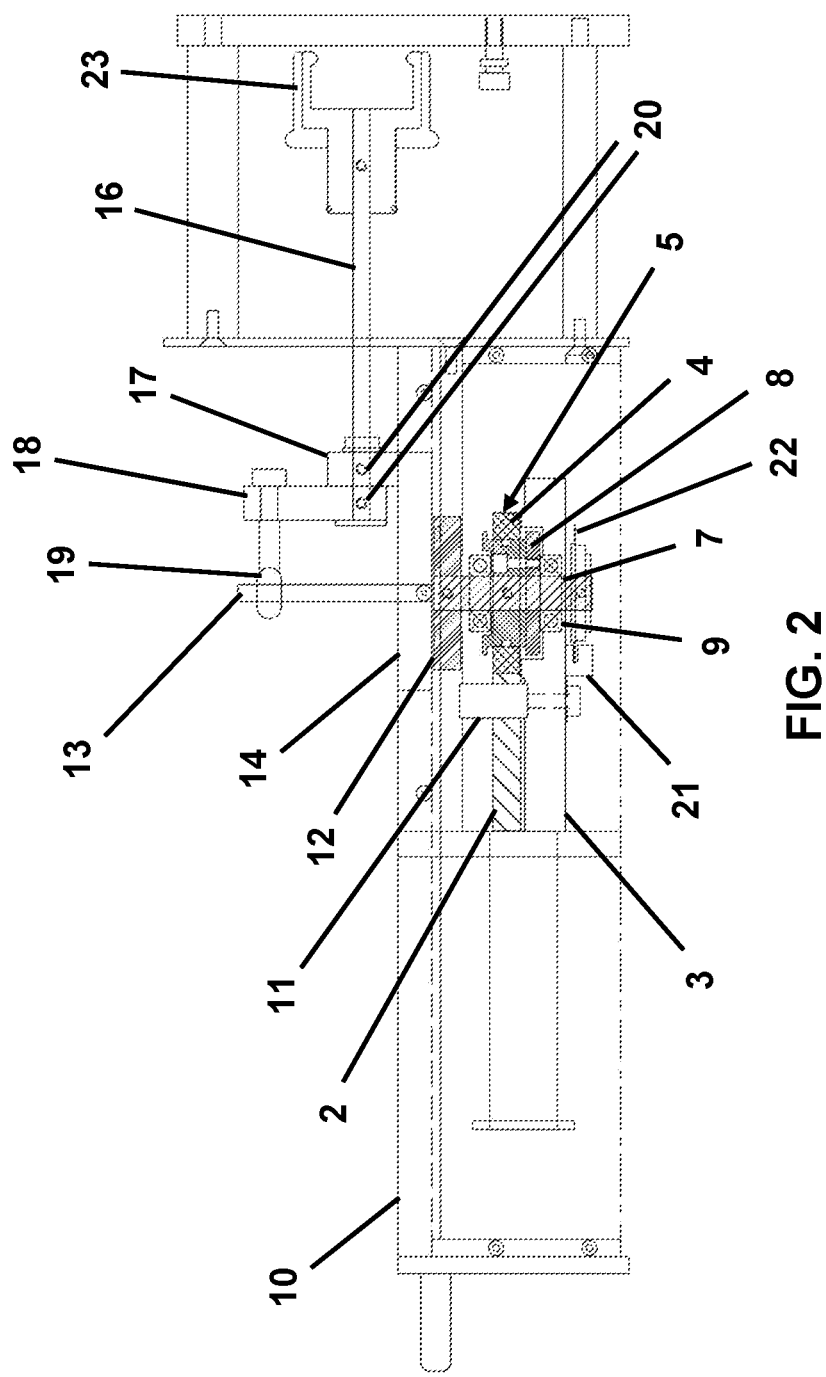
FIG. 2 is a schematic side view of the piezoelectric motor assembly.

As shown in FIGS. 1 and 2, the piezoelectric motor assembly 1 has at least two piezoelectric motors 2 mounted on a motor frame 3 about a circular body 4, which is rotatably mounted on the motor frame 3. The circular body 4 is a ring or disc-like structure, having a diameter, a thickness, and a circumferential outer surface 5. A ceramic ring is a preferred circular body 4 because it engages well with ceramic piezoelectric motors, but other materials may be used so as to match the circular body 4 with the piezoelectric motors 2 for efficient interaction therebetween.

The piezoelectric motors 2 are in tangential engagement with the outer surface 5 of the circular body 4 and cooperate with each other to drive the rotation of the circular body 4. Each piezoelectric motor 2 is biased against the outer surface 5 of the circular body 4, resulting in an unbalanced net force on the circular body 4 sufficient to pre-load the circular body 4. Preferably, linear walk piezoelectric motors are used to provide adequate speed and torque, but other types of piezoelectric motors may be used, such as ultrasonic resonant piezoelectric motors for optimizing speed or mini-inertia piezoelectric motors for minimizing size and maximizing torque.

Figure 3:
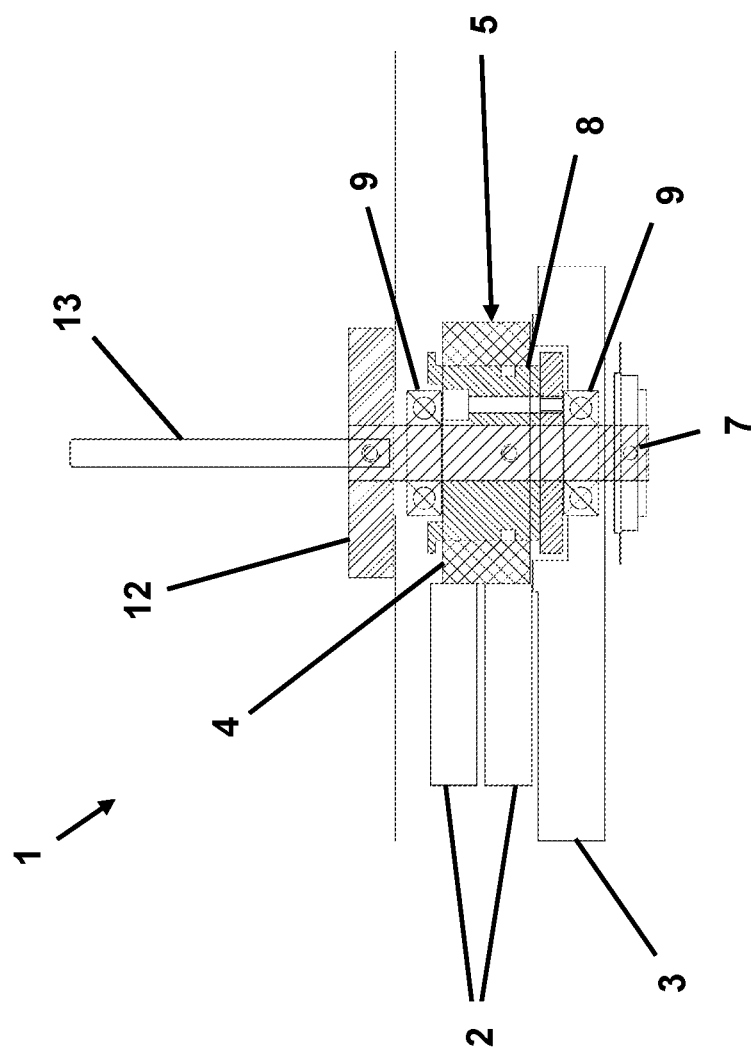
FIG. 3 is a detail view of an embodiment of the piezoelectric motor assembly.
Figure 5:
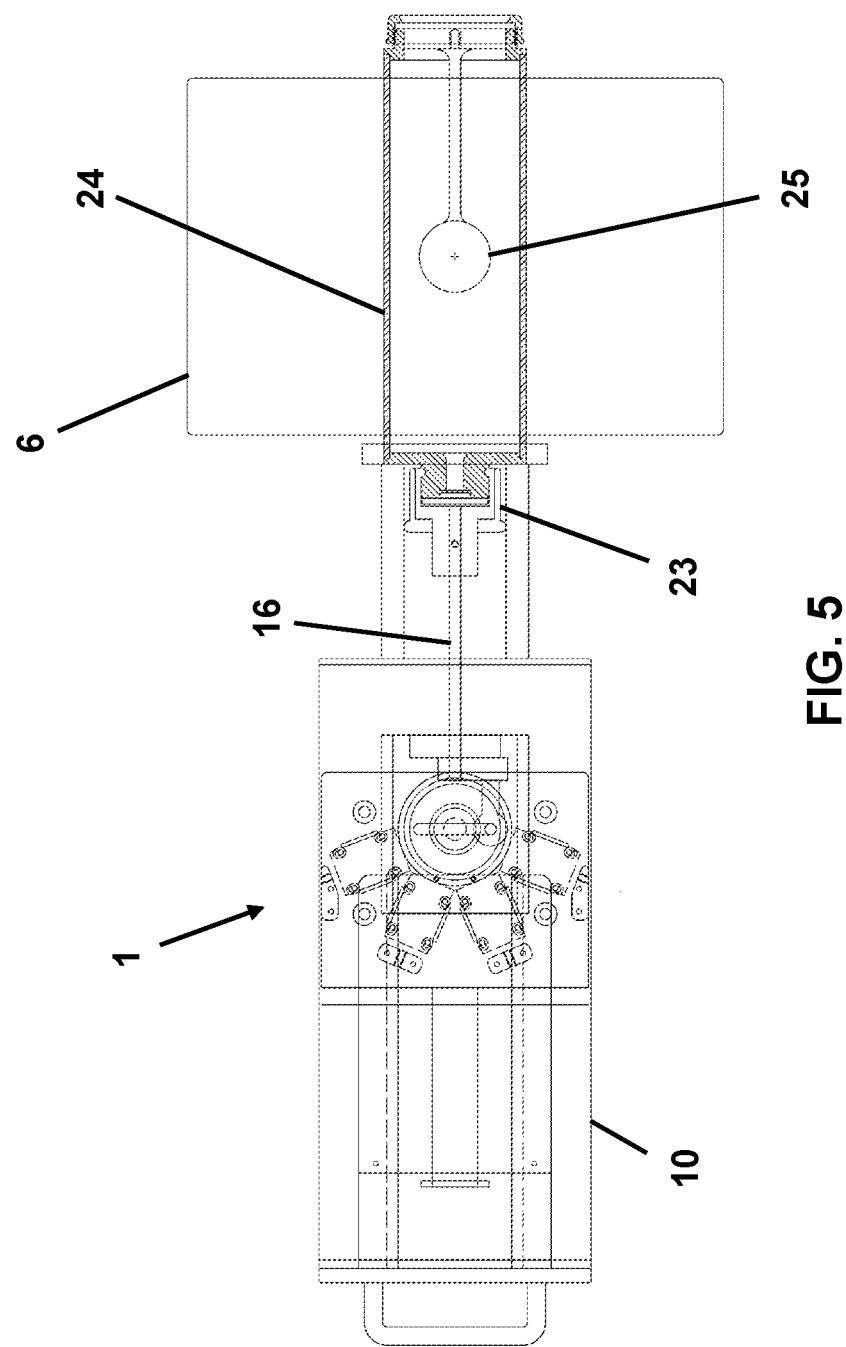
FIG. 5 is a schematic top view of the piezoelectric motor assembly, in combination with a MRI motion phantom.

Preferably, as shown in FIGS. 1 and 5, the piezoelectric motor assembly 1 has four piezoelectric motors 2, which are horizontally spaced apart on the outer surface 5 of the circular body 4. The piezoelectric motors 2 may be spread evenly about an arc subtending an angle of less than 180 degrees about the circular body 4. For example, the subtended angle between each of the four piezoelectric motors 2 may be less than 50 degrees and, preferably, the subtended angle is 46 degrees. Preferably, the subtended angle, and therefore the spacing, between piezoelectric motors 2 is minimized. Alternatively, or additionally, the piezoelectric motors 2 may be vertically spaced apart on the outer surface 5 of the circular body 4, as shown in FIG. 3.

Figure 4:
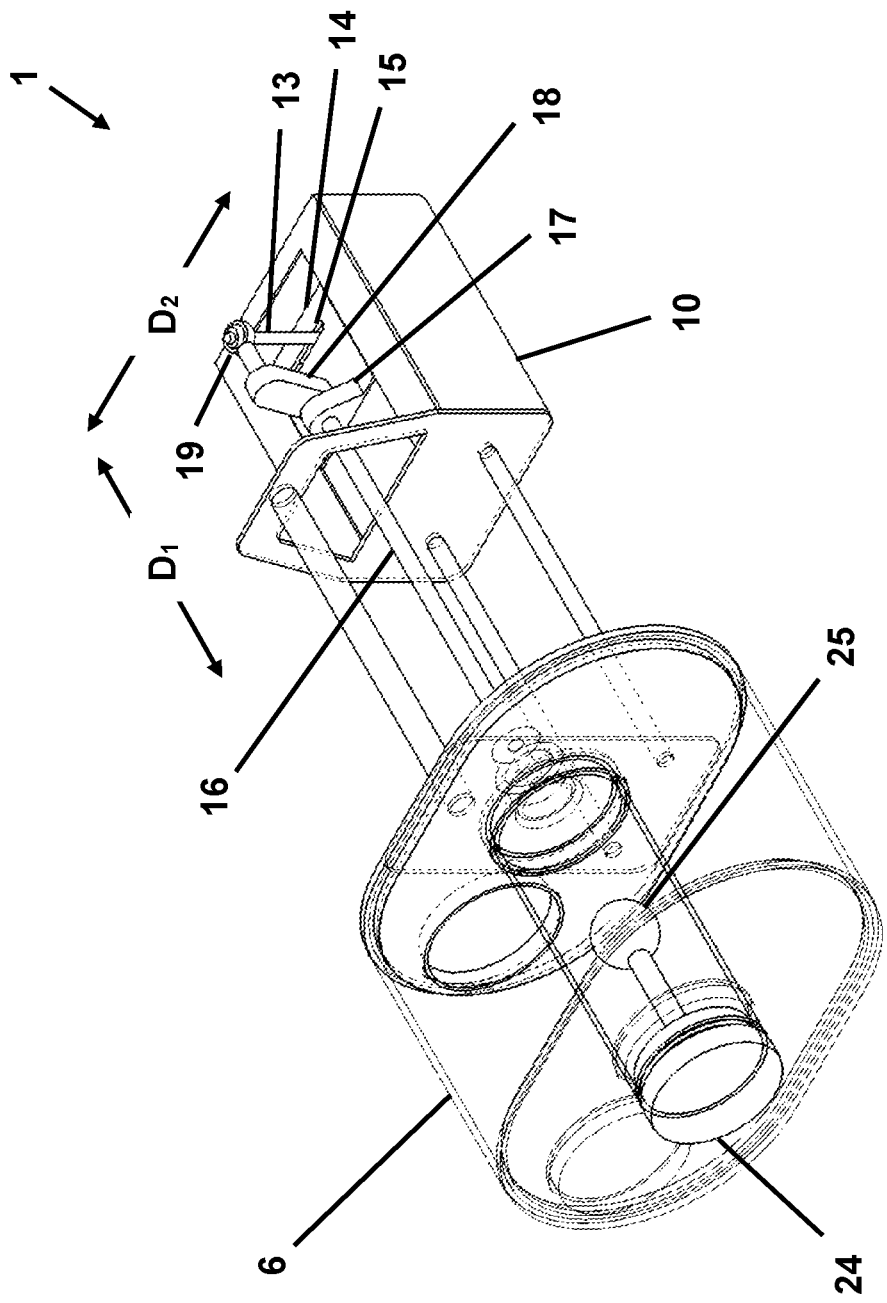
FIG. 4 is a perspective view of the piezoelectric motor assembly, in combination with a MRI motion phantom.

The piezoelectric motors 2 thereby power rotation of the circular body 4, which may be used to drive motion in various applications, requiring non-ferrous and non-magnetic motion control. One example of such an application is the combination of the piezoelectric motor assembly 1 and a MRI motion phantom 6, for use in a MRI system. In this embodiment, as shown in FIGS. 4-6, the rotary motion of the circular body 4 is converted into linear motion and, optionally, rotary motion by way of a motion translation mechanism to simulate anatomical motion in the MRI motion phantom 6.

Figure 6:
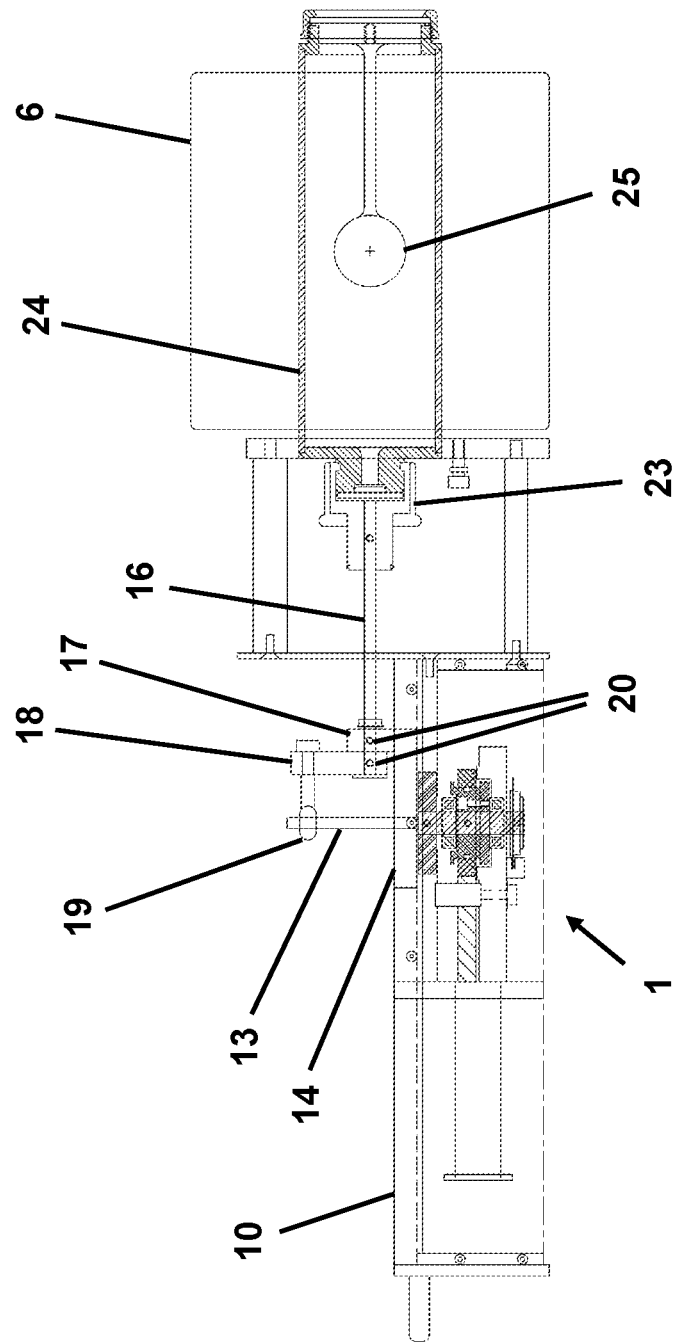
FIG. 6 is a schematic side view of the piezoelectric motor assembly, in combination with a MRI motion phantom.

As shown in FIGS. 2 and 6, the circular body 4 is mounted on a drive shaft 7 by way of a coupler 8. Two bearings 9 above and below the circular body 4 hold the drive shaft 7 in place. The top bearing is attached to the housing 10 of the piezoelectric motor assembly 1, while the bottom bearing is attached to the motor frame 3, which in turn is attached to the housing 10 by way of four support posts 11.

A drive hub 12 is attached at the top of the drive shaft 7 having a generally circular disc-like shape. A drive pin 13 is attached to the top of the drive hub 12 and is positioned off-centre on the drive hub 12 so as to travel in a circular path as the drive hub 12 is rotated by the cooperative action of the piezoelectric motors 2 on the outer surface 5 of the circular body 4. A translation stage 14 having a slot-like aperture 15 therethrough is slidably mounted to the housing 10, above the drive hub 12. The drive pin 13 extends upwardly through the slot-like aperture 15 in the translation stage 14 so as to move the translation stage 14 reciprocally in a first direction $D_1$ as the drive hub 12 rotates. The slot-like aperture 15 is oriented perpendicular to the first direction $D_1$ and the drive shaft 7.

A spindle 16 is rotatably mounted on the translation stage 14 by way of a rotary bearing 17 that extends upwardly from the translation stage 14 and holds the spindle 16 in place relative to the translation stage 14, but allows it to rotate feely. The spindle 16 is oriented axially in the first direction $D_1$, so as to move axially with the translation stage 14.

As shown in FIGS. 2 and 4, a pivot arm 18 is attached at one end to the spindle 16 adjacent to the rotary bearing 17. The other end of the pivot arm 18 is attached to the drive pin 13 by way of a ball joint 19. The pivot arm 18 pivots side to side, in a second direction $D_2$ perpendicular to the first direction $D_1$, as the drive pin 13 moves within the slot-like aperture 15 in the translation stage 14. The pivot arm 18 thereby rotates the spindle 16 as it moves axially on the translation stage 14. Set screws 20 may be used to selectively lock the spindle 16 rotationally within either the end of the pivot arm 18, or alternatively within the rotary bearing 17. If the spindle 16 is locked rotationally within the end of the pivot arm 18 and free to rotate within the rotary bearing 17, the spindle 16 will rotate as it moves axially under the forces applied by the drive pin 13. If the spindle 16 is locked rotationally within the rotary bearing 17 and free to rotate within the end of the pivot arm 18, it will not rotate and will only move axially.

The piezoelectric motors 2 are controlled by a closed-loop piezoelectric motor drive control unit (not shown). An encoder 21 is used to provide position information to the control unit, to enable the control unit to track and account for the rotational position of the drive shaft 7 during operation. As shown in FIG. 2, an optical encoder 21, which uses an optical reader to count gradings on a glass ring 22 attached to the drive shaft 7, may be mounted below the motor frame 3.

In applications, such as inside a MRI system, where ferrous materials are unsuitable and/or dangerous, all of the elements of the piezoelectric motor assembly 1 are made of ceramic, plastic, or non-ferrous metal to permit use inside the MRI system and to avoid causing imaging artifacts. The housing 10 may also be provided with RF shielding, designed for minimal interaction with static and time varying gradient magnetic fields.

In operation, the control unit actuates the piezoelectric motors 2 to cooperatively drive the rotation of the circular body 4, which in turn rotates the drive shaft 7. The drive hub 12, on the end of the drive shaft 7 rotates, thereby moving the drive pin 13 in a circular motion within the slot-like aperture 15 of the translation stage 14, which converts the circular motion of the drive pin 13 into linear motion in a first direction $D_1$. The pivot arm 18 is attached to the drive pin 13 by way of a ball joint 19, so as to covert the motion of the drive pin 13, within the slot-like aperture 15, into rotational motion. The spindle 16 is attached to, and moves reciprocally with, the translation stage 14 and also selectively receives rotation from the pivot arm 18.

As shown in FIGS. 5 and 6, the other end of the spindle 16 is attached by way of a mechanical quick-release clasp 23 to an insert 24, such as a hollow, fluid, or MRI gel filled cylindrical insert. The insert 24 is slidably and rotatably mounted within the MRI motion phantom 6, which may be a torso or thorax shaped hollow or fluid filled phantom that may act as a surrogate for anatomical shapes. This type of MRI motion phantom 6 may be used to simulate the thorax of a breathing patient. The insert 24 may be selected to provide similar imaging properties to human lung tissue and may have a tumour model target 25 with different imaging properties at a known location therein. Other types and configurations of motion phantoms may be used to simulate anatomical motion for other applications and/or regions of the body.

This type of MRI motion phantom 6 typically uses an insert 24 weighing up to 1 kg. Testing parameters may require that such an insert 24 be moving back and forth within the MRI motion phantom 6 at up to 60 times per minute, for example to simulate a patient's lung movement while the patient is hyperventilating. These operating parameters require higher speed and torque than presently available rotary piezoelectric motor assemblies are capable of providing. Some embodiments of the piezoelectric motor assembly 1, according to the present invention, are able to meet these parameters.

For higher load or speed requirements, additional piezoelectric motors 2 may be added by pairing them with the original piezoelectric motors 2 and positioning them on top of one another. Each pair of piezoelectric motors 2 is then controlled and acts together on the circular body 4 to increase the speed and/or torque of the piezoelectric motor assembly 1.

For compact design requirements, at least two piezoelectric motors 2 may be vertically spaced apart on the outer surface 5 of the circular body 4 and vertically aligned parallel to the central axis of the drive shaft 7 to provide an effective single point source tangential load against the circular body 4.

The maximum speed and torque achievable by the piezoelectric motor assembly 1 is also dependent on the diameter of the circular body 4. Generally, as the diameter increases, the torque increases and the speed decreases, and vice versa. Accordingly, the diameter of the circular body 4 may be varied according to the desired speed and torque requirements for a particular application.

The entire assembly of the piezoelectric motor assembly 1 and the MRI motion phantom 6 is placed within a MRI system and controlled, during operation of the MRI system, to provide precise motion within known dimensions and speed parameters. This may be used to test the MRI system's imaging equipment for real time 4D imaging to ensure its ability to accurately track the position of a moving target inside the MRI system.

A number of embodiments of the present invention have been described and shown in the accompanying drawings. Nonetheless, the embodiments are described herein illustratively and are not meant to limit the scope of the invention, as claimed. Variations of the foregoing embodiments will be evident to a person of ordinary skill and are intended by the inventor to be encompassed by the following claims.

What is claimed is:

1. A piezoelectric motor assembly for producing rotary motion, comprising:
   a motor frame;
   a circular body rotatably mounted on the motor frame, having a diameter, a thickness, and a circumferential outer surface; and
   at least two piezoelectric motors mounted on the motor frame in tangential engagement with the outer surface of the circular body; and
   wherein the at least two piezoelectric motors are biased against the outer surface to result in an unbalanced net force on the circular body.

2. The piezoelectric motor assembly of claim 1, wherein the at least two piezoelectric motors are horizontally spaced apart on the outer surface of the circular body.

3. The piezoelectric motor assembly of claim 2, wherein the at least two piezoelectric motors are horizontally spaced apart along an arc subtending an angle of less than 180 degrees.

4. The piezoelectric motor assembly of claim 3, wherein at least two piezoelectric motors comprises three piezoelectric motors.

5. The piezoelectric motor assembly of claim 3, wherein the at least two piezoelectric motors comprises four piezoelectric motors.

6. The piezoelectric motor assembly of claim 5, wherein the subtended angle between each piezoelectric motor is less than 50 degrees.

7. The piezoelectric motor assembly of claim 6, wherein the subtended angle between each piezoelectric motor is 46 degrees.

8. The piezoelectric motor assembly of claim 3, wherein the at least two piezoelectric motors are linear walk piezoelectric motors.

9. The piezoelectric motor assembly of claim 1, wherein the at least two piezoelectric motors are vertically spaced apart on the outer surface of the circular body.

10. The piezoelectric motor assembly of claim 9, wherein the at least two piezoelectric motors comprises three piezoelectric motors.

11. The piezoelectric motor assembly of claim 9, wherein the at least two piezoelectric motors comprises four piezoelectric motors.

12. The piezoelectric motor assembly of claim 9, wherein the at least two piezoelectric motors are linear walk piezoelectric motors.

13. The piezoelectric motor assembly of claim 9, wherein the at least to piezoelectric motors are aligned parallel to the drive shaft.

14. The invention of claim 1 in combination with a MRI motion phantom having a slidable and rotatable MRI insert, comprising:
   a drive hub rigidly attached to the circular body, having an off-centre drive pin extending upwardly therefrom;
   a spindle operatively connected with the drive pin by way of a motion translation mechanism to translate the rotational motion of the drive pin into reciprocal linear and rotational motion of the spindle; and
   a MRI motion phantom containing a first MRI signal producing material and having an aperture therethrough for receiving a MRI insert; and
   a MRI insert containing a second MRI signal producing material and attached to the spindle and slidably and rotatably mounted within the aperture in the MRI motion phantom.

* * * * *